United States Patent [19]

Hinton et al.

[11] 4,368,166

[45] Jan. 11, 1983

[54] METHOD FOR THE PRODUCTION OF A CERAMIC INSULATOR

[75] Inventors: Jonathan W. Hinton, Birmingham; Frederick J. Powell, East Detroit; Robert W. Matz, Troy, all of Mich.

[73] Assignee: Champion Spark Plug Company, Toledo, Ohio

[21] Appl. No.: 295,935

[22] Filed: Aug. 24, 1981

Related U.S. Application Data

[63] Continuation of Ser. No. 85,505, Oct. 17, 1979, abandoned.

[51] Int. Cl.³ .............................................. C04B 37/00
[52] U.S. Cl. ..................................... 264/61; 174/209; 264/56; 264/60
[58] Field of Search .............................. 264/60, 61, 56

[56] References Cited

U.S. PATENT DOCUMENTS

| 1,342,398 | 6/1920 | Sperry. | |
|---|---|---|---|
| 2,331,748 | 10/1943 | Tognola | 123/169 |
| 2,449,403 | 9/1948 | McDougal | 123/169 |
| 2,783,409 | 2/1957 | McDougal | 313/141 |
| 4,013,746 | 3/1977 | Goreham et al. | 264/66 |
| 4,193,857 | 3/1980 | Bannister et al. | 264/61 |
| 4,248,813 | 2/1981 | Hattori et al. | 264/60 |

FOREIGN PATENT DOCUMENTS 968768  3/1958  Fed. Rep. of Germany.

OTHER PUBLICATIONS

Champion Spark Plug Company, 1973 Engineering Manual, p. 17 and attached photograph.

Primary Examiner—James H. Derrington
Attorney, Agent, or Firm—John C. Purdue

[57] ABSTRACT

A ceramic insulator and a method for the production thereof are disclosed. The method comprises the steps of pressing ceramic batch around a contoured arbor having at least two longitudinally extending fins to form an outer piece having a bore with grooves therein corresponding to the fins, removing the arbor from and contouring the piece to a desired external shape, pressing ceramic batch to form an inner piece, and contouring the inner piece to fit within the bore of the outer piece. The inner piece is then positioned within the bore of the outer piece and both pieces are fired whereby the insulator is produced in which the contoured surface of the inner piece closes the grooves in the bore of the outer piece to form slots extending longitudinally within the ceramic insulator. Also disclosed is a method which involves firing the inner piece, positioning the fired inner piece within the bore of the unfired outer piece, and then firing both pieces together. A ceramic insulator according to the invention is useful as a support for an oxygen sensor which can be placed in the exhaust gases from an internal combustion engine and used to measure oxygen content thereof to enable control of the air-fuel ratio at which the engine is operated so that, for example, emissions can be minimized.

2 Claims, 17 Drawing Figures

U.S. Patent    Jan. 11, 1983    Sheet 1 of 4    4,368,166
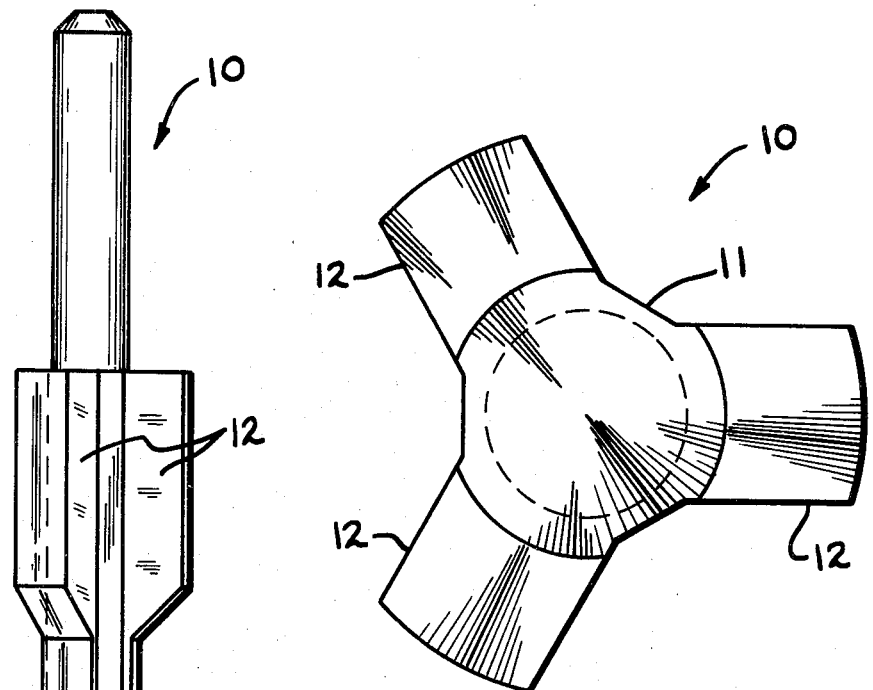
FIG. 2
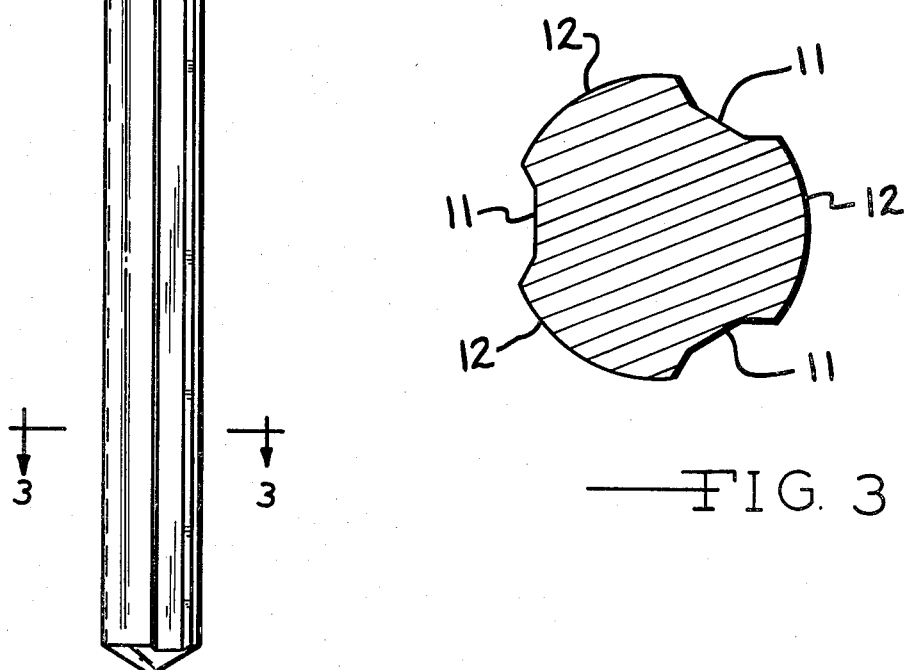
FIG. 3
FIG. 1

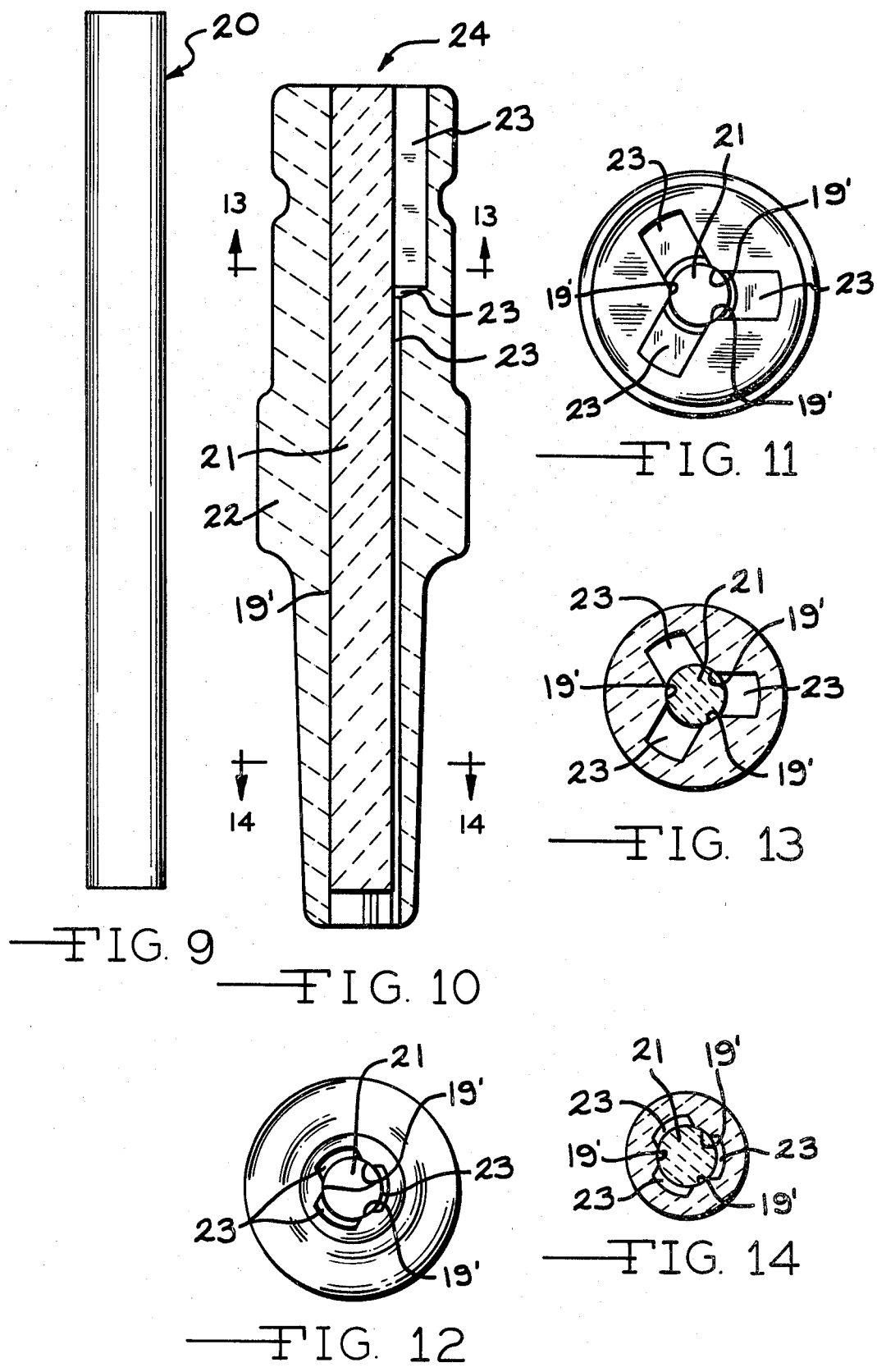

METHOD FOR THE PRODUCTION OF A CERAMIC INSULATOR

This is a continuation, of application Ser. No. 85,505 filed Oct. 17, 1979, now abandoned

BACKGROUND OF THE INVENTION

Ceramic insulators have been produced by pressing ceramic batch to form a piece which can be contoured to a desired external shape. A bore extending longitudinally of the piece can be formed by pressing the ceramic batch around an arbor. However, when a need arose for a ceramic piece having a plurality of bores or internal slots extending longitudinally thereof for forming an insulator to be used as a part of an oxygen sensor, no method other than extrusion and subsequent drilling, complex injection molding, or multi-stage precision drilling was available.

BRIEF DESCRIPTION OF THE INVENTION

The instant invention is based upon the discovery of a method which involves pressing ceramic batch to form two ceramic pieces which are assembled to form a ceramic insulator having longitudinally extending internal slots therein. Rather than separately machining the slots, the method comprises pressing ceramic batch around a contoured arbor having at least two longitudinally extending fins to form an outer piece having a complex bore with grooves therein corresponding to the fins*, removing the arbors from the outer piece, forming ceramic batch to make an inner piece, and contouring the inner piece to fit within the bore of the outer piece. The inner piece is then positioned within the bore of the outer piece. Both pieces are fired together whereby the contoured surface of the inner piece closes the grooves in the complex bore of the outer piece to form slots extending longitudinally within the ceramic insulator. The desired article can also be produced by firing the inner piece before it is positioned within the bore of the outer piece.

*Such ceramic pieces have previously been made by the indicated method and, after firing, have been assembled into "thermocouple spark plugs" where thermocouples to measure temperature while the spark plugs were in operating engines were installed in the grooves.

OBJECTS OF THE INVENTION

It is an object of the invention to provide an improved method for producing a ceramic insulator having longitudinally extending internal slots therein.

It is a further object of the invention to provide a ceramic insulator having longitudinally extending internal slots therein.

BRIEF DESCRIPTION OF THE DRAWINGS

FIG. 1 is a side view in vertical elevation of an arbor which can be used in practicing the present invention.

FIG. 2 is a bottom view of the arbor of FIG. 1.

FIG. 3 is a sectional view through the arbor taken on the line 3—3 of FIG. 1.

FIG. 9 is a view in vertical elevation of an unfired inner piece which can be used in producing a ceramic insulator in accordance with the invention.

FIG. 10 is a vertical sectional view of a ceramic insulator in accordance with the invention, and comprising an inner piece of FIG. 9 disposed within an outer piece of FIGS. 4 through 8.

FIG. 11 is a top view of the ceramic insulator of FIG. 10.

FIG. 12 is a bottom view of the ceramic insulator of FIG. 10.

FIG. 13 is a sectional view through the ceramic insulator taken on the line 13—13 of FIG. 10.

FIG. 14 is a sectional view through the ceramic insulator taken on the line 14—14 of FIG. 10.

DETAILED DESCRIPTION OF THE INVENTION

Referring to FIG. 1, an arbor indicated generally at 10 comprises a cylindrical mandrel 11 having three fins 12 (see FIGS. 2 and 3) extending longitudinally thereof. The three fins 12 are equally spaced 120° on centers around the mandrel 11, a preferred structure because of the comparatively simple geometry; however, asymmetrical spacing thereof, a positioning notch (see FIGS. 15-17) or the like is sometimes desirable so that an oxygen sensor can be assembled in an oriented manner with an insulator formed around the arbor 10.

Figure 4:
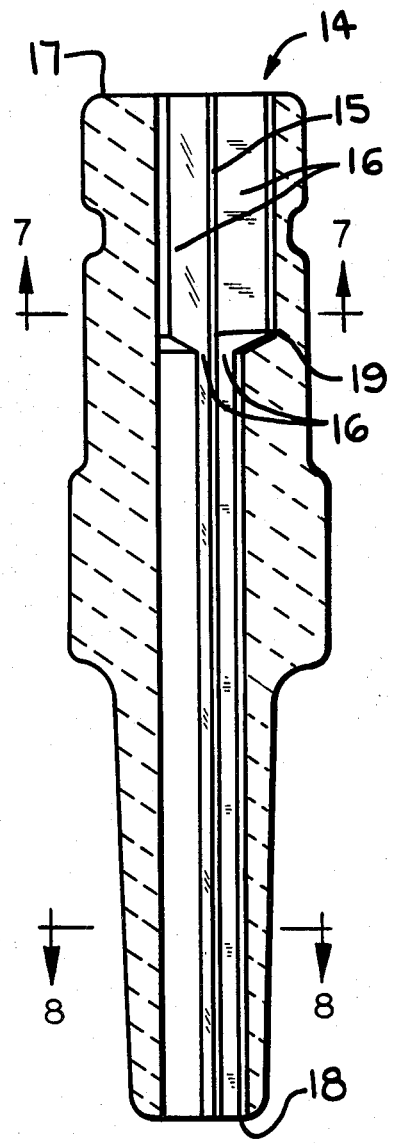
FIG. 4 is a vertical sectional view of an outer piece which can be formed around the arbor of FIGS. 1-3 and used in producing a ceramic insulator in accordance with the invention.
Figure 6:
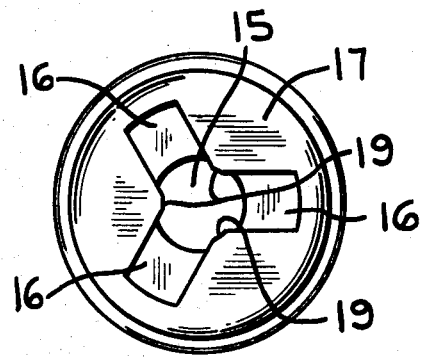
FIG. 6 is a top view of the outer piece of FIG. 4.
Figure 7:
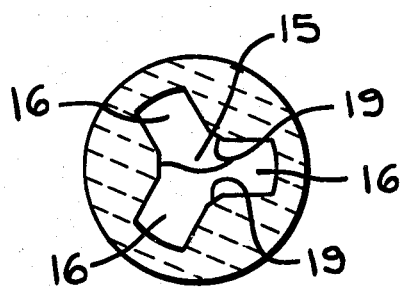
FIG. 7 is a sectional view through the outer piece taken on the line 7—7 of FIG. 4.
Figure 8:
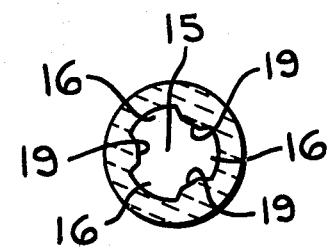
FIG. 8 is a sectional view through the outer piece taken on the line 8—8 of FIG. 4.
Figure 5:
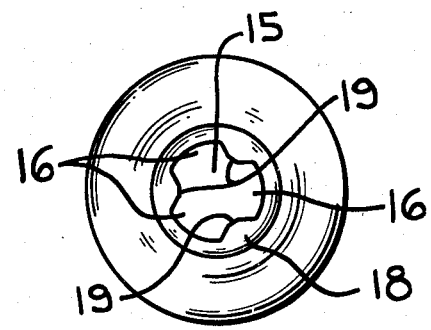
FIG. 5 is a bottom view of the outer piece of FIG. 4.

The first step in producing an outer insulator piece, indicated generally at 14 in FIG. 4, of an insulator according to the invention involves pressing, preferably isostatically, ceramic batch around the contoured arbor 10 (FIG. 1). The piece 14 (FIG. 4) has a bore 15 formed around the mandrel 11, and extending the entire length thereof, and grooves 16 formed by the fins 12 of the arbor 10 (FIG. 1); the grooves 16 extend the entire length of the walls of the bore 15, tapering at an intermediate point from a maximum depth at an insulator end 17 to a minimum depth at an insulator end 18. The innermost walls 19 of the bore 15 are formed around the mandrel 11 between each of the three grooves 16. After the piece 14 is formed therearound, the arbor 10 is removed from the outer piece 14, and the latter is contoured to a desired external shape.

Referring to FIG. 9, ceramic batch is pressed and contoured to form an inner insulator piece 20 having the general shape of the mandrel 11 to fit within the bore 15 of the outer piece 14 (FIG. 4). The contoured inner piece 20 is then positioned within the bore 15 of the outer piece 14 and both pieces are fired together. The relative dimensions of the innermost walls 19 of the bore 15 of the outer piece 14 and of the exterior walls of the inner piece 20 are such that the shrinkage of the two pieces during firing causes the surface of the inner piece, designated, after firing, 21 in FIGS. 10-14, to fit tightly against the shrunken innermost walls of the outer piece, designated 19' and 22, respectively, after firing, to form slots 23 extending longitudinally within a composite ceramic insulator which is indicated generally at 24 in FIG. 10.

Although the method described above can be used to produce an insulator according to the invention, the preferred method is to fire the inner piece 20 alone, to position the fired inner piece 21 within the bore 15 of the unfired outer piece 14, and to fire the resulting assembly made up of both pieces. The elevated temperature of firing causes the innermost walls 19' of the fired outer piece 22 to shrink tightly against the surface of the fired inner piece 21.

Figure 15:
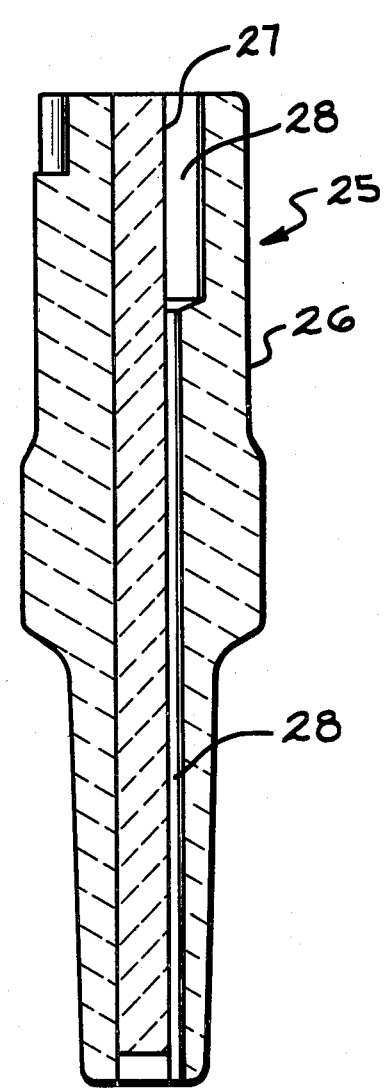
FIG. 15 is a vertical sectional view, similar to FIG. 10, of another and preferred ceramic insulator in accordance with the invention.
Figure 16:
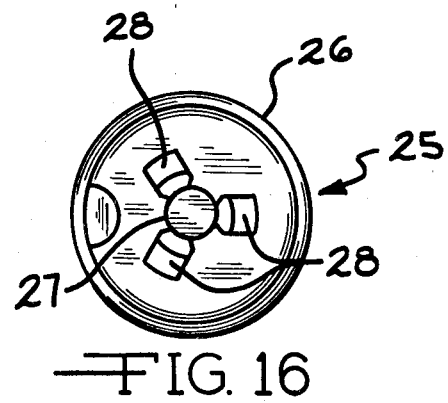
FIG. 16 is a top view of the ceramic insulator of FIG. 15.
Figure 17:
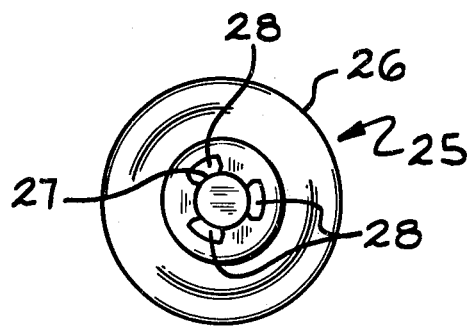
FIG. 17 is a bottom view of the ceramic insulator of FIG. 15.

The best presently known mode of an insulator according to the instant invention is indicated generally at 25 in FIGS. 15–17. The insulator 25 comprises an outer piece 26 and an inner piece 27, as well as slots 28 formed in the outer piece 26 and closed by the inner piece 27. The slots 28 decrease in diameter adjacent the inner piece 27, differing in this respect from the slots 23 in the insulator of FIGS. 10–14.

It will be apparent that various changes may be made from the details of the invention shown in the attached drawings and discussed in connection therewith without departing from the spirit and scope of this invention as defined in the appended claims. It is, therefore, to be understood that this invention is not to be limited to the specific details shown and described.

What we claim is:

1. A method for producing a ceramic insulator having at least two internal slots extending longitudinally of the insulator, said method consisting of the steps of pressing ceramic batch around a contoured arbor having at least two longitudinally extending fins to form an outer piece having a bore with grooves therein corresponding to the fins, removing the arbor from and contouring the outer piece to a desired external shape, pressing ceramic batch to form an inner piece, contouring the inner piece to fit within the bore of the outer piece, positioning the inner piece within the bore of the outer piece and firing both pieces, whereby the contoured surface of the inner piece closes the grooves in the bore of the outer piece to form slots extending longitudinally within the ceramic insulator.

2. A method as claimed in claim 1, wherein the inner piece is fired, the fired inner piece is positioned within the bore of the unfired outer piece, and the resulting assembly of the fired inner piece within the unfired outer piece is fired.

* * * * *